United States Patent [19]

Boissard et al.

[11] Patent Number: 5,055,470

[45] Date of Patent: Oct. 8, 1991

[54] METHOD OF TREATMENT OF ISCHEMIA IN BRAIN

[75] Inventors: Christopher G. Boissard, Northford; Duncan P. Taylor, Middletown; Michael S. Eison, Avon, all of Conn.

[73] Assignee: Bristol-Myers Squibb Co., New York, N.Y.

[21] Appl. No.: 360,658

[22] Filed: Jun. 1, 1989

[51] Int. Cl.$^5$ .............................................. A61K 31/505
[52] U.S. Cl. .................................... 514/252; 514/255
[58] Field of Search ........................ 514/225, 255, 252

[56] References Cited

U.S. PATENT DOCUMENTS 4,605,655  8/1986  Yevich et al. ......................... 514/252
4,711,899  12/1987  Gandillieri et al. ................... 514/330

OTHER PUBLICATIONS

Wauquier et al., in "Drug Development Research", 8, pp. 373–380, (6/9).
SCRIP (#1314–1315), pp. 30–31 (Jun. 3–8, 1988).
Barnes, *Science*, vol. 235, pp. 632–633; (2/6/87) (5/19).
Simon in "Frontiers in Excitatory Amino Acid Research", pp. 639–644, (6/2).
Gotti et al., *JPET*, 247/3, pp. 1211–1221; (1988) (6/4).

*Primary Examiner*—Mukund J. Shah
*Assistant Examiner*—Edward C. Ward
*Attorney, Agent, or Firm*—Richard P. Ryan

[57] ABSTRACT

A process for protecting brain cells from ischemia and for treating ischemic and degenerative brain disorders. The process involves systemic administration of BMY 14802 or a pharmaceutically acceptable acid addition salt and/or hydrate.

11 Claims, No Drawings

METHOD OF TREATMENT OF ISCHEMIA IN BRAIN

FIELD OF THE INVENTION

This invention is concerned with a drug bio-affecting body-treating process which employs the piperazinyl butyrophenone compound 4-[4-(5-fluoro-2-pyrimidinyl)-1-piperazinyl]-1-(4-fluorophenyl)butanol or a pharmaceutically acceptable acid addition salt thereof.

BACKGROUND OF THE INVENTION

The piperazinyl butyrophenone compound with which the present inventive method is concerned has been referred to in the prior art as BMY 14802 and also MJ 14802. The synthesis of the compound and a disclosure of its antipsychotic properties are described by Yevich, et al., in U.S. Pat. No. 4,605,655.

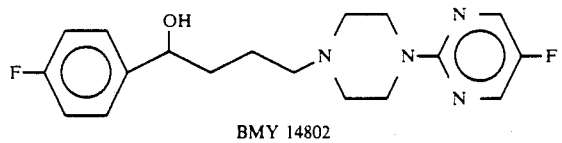

BMY 14802

Brain cells are particularly vulnerable to damage caused by ischemic conditions. Brain ischemia, or insufficient oxygen, may result from injury or disease and may last from only transient periods of time to periods of lengthy duration, as in stroke or following cardiac arrest. The principle disease associated with brain ischemia is ischemic cerebral vascular disease (ICVD), and in general refers to the disorders resulting from an insufficient supply of blood, with its nourishing oxygen content, to brain areas.

Seizures and stroke are two frequent manifestations of ischemic cerebral vascular disease. There can be many underlying causes of cerebral vascular ischemia, with several of the more common listed below;

Atherosclerosis—the most common underlying condition and may be caused either by hemodynamic or thromboembolic mechanisms.

Hypertension—can impair cardiac function and/or alter cerebral circulation.

Cardiac disease—comprises such disorders as cardiac arrhythmias, congestive heart failure, myocardial infarction, and the like.

Hematologic disorders—increased viscosity of blood or other deleterious blood alterations.

Arteritis—inflammation of intracranial arteries, may be of either infective or noninfective origin.

Head injury—injuries compromising cerebral blood supply or altering the cerebral circulation.

Vasospasm—decreased blood flow due to constrictive spasms of the vasculature.

As a result of ischemia in the cerebral vasculature, various clinical disorders may result. These disorders may range from transient ischemic attacks to a permanently disabling stroke. Transient ischemic attacks (TIAs) are brief (usually less than one hour) spells characterized by symptoms referable to vascular territories in the retinal, carotid, or vertibrobasilar circulation. These spells indicate a high risk for subsequent stroke, a serious disorder of more lengthy duration. Stroke, also called "cerebral vascular accident" or "cerebral crisis" refers to a sudden apoplectic attack ordinarily due to cerebral infarction, hemorrhage, or vasospasm and usually characterized by some degree of paralysis. The immediate 72 hours following stroke onset is a critical time interval since the degree of brain damage suffered may be reversible to some extent if the anoxic conditions can be eased. When the brain is deprived of oxygen, due to stroke, heart attack, or other cause; nerve damage can become irreversible and virtually untreatable. It is one object of this invention to prevent the nerve cell damage caused by ischemia. Current methods for treating stroke and brain ischemia necessarily focus on preventing hypoxia and restoring adequate blood circulation. There are no accepted methods for protecting brain cells subjected to ischemic conditions.

Various therapies have been employed in efforts to treat acute strokes and prevent significant persisting neurological deficits. Types of agents employed have been vasodilators, such as papaverine, prostacyclin, and pentoxifylline; hemodilution agents, thrombolytic agents such as tissue plasminogen activator (TPA) and calcium channel blockers; and anticoagulants such as heparin or warfarin. Transient ischemic attacks are generally treated with either anticoagulants or antiaggregators such as aspirin.

There are, at present, no effective, approved treatments which may be used therapeutically and/or prophylactically to minimize the brain cell damage caused by ischemic conditions. It is an objective of this invention to provide such a treatment that will protect brain cells from ischemia-induced damage.

Several compounds have been disclosed as being under study as potential protective agents for anoxic brain cells.

An experimental drug, MK-801, is being studied to determine its effectiveness in limiting neuronal injury after ischemia (Barnes, *Science*, VOL. 235, pp 632-633, Feb. 6, 1987).

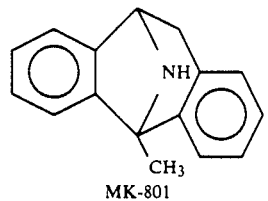

MK-801

Dextromethorphan, the non-narcotic cough suppressant, and ketamine have also been disclosed as being effective in protecting brain cells under anoxic conditions by Simon in "Frontiers in Excitatory Amino Acid Research", pages 639-644, © 1988 Alan R. Liss, Inc.

Gotti, et al., *JPET.* 247/3, pages 1211-1221 (1988); have disclosed that ifenprodil and a derivative are effective in tissue sparing in animal models of stroke and brain infarction.

IFENPRODIL

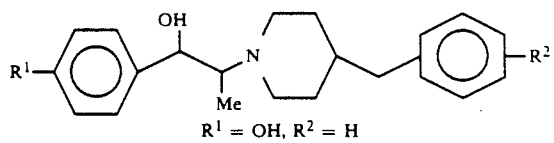

$R^1 = OH, R^2 = H$

Wauquier, et al., in "Drug Development Research", 8/373-380 (1986) disclosed that Sabeluzole (R 58,735) is a potent antihypoxic agent with anticonvulsant properties.

SABELUZOLE

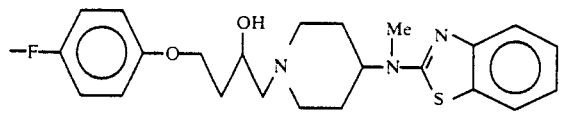

A series of anti-anoxic 2-[4-benzoyl-1-piperidinyl]-1-phenylalkanol derivatives, having some structural resemblance to ifenprodil type compounds, is disclosed in U.S. Pat. No. 4,711,899 issued in December, 1987 to Gaudilliere, et al.

There is nothing in these references, or in the general prior art, to suggest the method of the present invention—that administration of BMY 14802 would effectively protect brain cells against ischemia.

SUMMARY OF THE INVENTION

The method of the present invention is intended for protecting brain cells, particularly neurons, against the effects of ischemia which may result from stroke and other brain traumas, which can lead to clinical disorders such as paralysis, aphagia, and seizures. The method is also applicable to certain brain degenerative processes. The method essentially involves administration of BMY 14802, 4-[4-(5-fluoro-2-pyrimidinyl)-1-piperazinyl]-1-(4-fluorophenyl)butanol, or a pharmaceutically acceptable salt and/or hydrate thereof, to a mammal in need of such treatment.

DETAILED DESCRIPTION OF THE INVENTION

Development of an ischemic environment for brain tissue leads to a degenerative anoxic cascade process which results in brain damage. In the U.S. an estimated 500,000 persons suffer their first stroke each year. Once stroke has occurred, very little can be done currently. It is also estimated that for each 100 patients that survive a stroke attack, approximately only 10 will recover normal functioning, 40 will suffer mild impairment, 40 will suffer moderate impairment and 10 will be so severely impaired that they will require institutionalization. From the standpoint of a medical practitioner, an agent which would acutely or prophylactically protect brain cells from the degenerative anoxic cascade resulting from ischemia would be highly prized. No such agent is approved for clinical use at the present time and the therapies which are employed are directed mainly to assisting or restoring blood flow to the brain.

The present invention results from the discovery that BMY 14802 exhibits activities in certain pharmacologic tests and model systems that are used to determine drug effects on brain ischemia and its aftermath. Specifically, BMY 14802 administration results in:

raising the seizure threshold for N-methyl-D-aspartic acid (NMDA), an excitatory amino acid which activates a subclass of glutamate receptors in the brain. The excitatory neurotransmitter glutamate is believed to act as a neurotoxic agent following ischemia.

protecting against a model of hypoxia-induced death in rats.

antagonizing the NMDA-evoked release of acetylcholine.

Taken together, these data demonstrate that BMY 14802 is an effective prophylactic and therapeutic treatment for protection and salvage of brain cells from ischemic degenerative processes. In this regard BMY 14802 represents a significant advantage over other agents used to treat ischemia-induced brain damage.

Consideration of test results obtained for BMY 14802 indicates usefulness in several specific clinical applications wherein such ischemia-protecting effects on brain cells would be highly desirable. The subject compound is intended for use in transient ischemic attacks; stroke; multi-infarct dementia; seizures, including some forms of epilepsy; hypoglycemia; preoperative treatment; anoxia, such as that caused by cardiac disease, e.g. myocardial infarction, congestive heart failure, etc.; asphyxiation; brain injury and trauma. Due to the ability of BMY 14802 to antagonize NMDA-evoked acetylcholine release, BMY 14802 appears to possess the potential to inhibit the release of anoxia-related neurodegenerative agents such as the excitatory amino acids glutamate and aspartate. BMY 14802 is also intended for use in certain brain degenerative disorders such as Alzheimer's disease, Parkinson's disease, Huntington's disease, olivopontocerebellar atrophy and amylotrophic lateral sclerosis. In general, BMY 14802 should be useful for those brain disorders whose underlying etiology involves ischemia and/or the resulting anoxia-induced neurodegenerative cascade. Such clinical applications would be known to one skilled in the medical arts. An illustrative example of a clinical application would be the use of BMY 14802 in seizures. Seizures and some epilepsies can be caused by anoxia, cerebrovascular disease, neurodegenerative processes or head injury and trauma. A more detailed description can be found in "Drug Evaluation, 6th Edn.", AMA, W. B. Saunders Co., Phil. Pa., 169-176.

The compound BMY 14802 is also useful for treatment and prevention of injury to the brain and spinal cord and of edema due to head trauma, stroke, arrested breathing, cardiac arrest, Reye's syndrome, cerebral thrombosis, embolism, hemorrhage or tumors, encephalomyelitis, spinal cord injury, hydrocephalus and postoperative brain injury.

The process of the present invention then essentially involves administration of BMY 14802 or a pharmaceutically acceptable salt and/or hydrate thereof, to a mammal suffering from ischemia or being susceptible to ischemia. Synthesis of BMY 14802, its pharmaceutically acceptable acid addition salts and methods of pharmaceutical formulation and administration are described in the patent of Yevich, et al., U.S. Pat. No. 4,605,655 which is incorporated herein in its entirety by reference. In accordance thereto, each enantiomeric form of BMY 14802 and mixtures thereof are also intended.

Although the dosage and dosage regimen of BMY 14802 must in each case be carefully adjusted, utilizing sound professional judgment and considering the age, weight and condition of the recipient, the route of administration and the nature and extent of the ischemia, generally, the daily dose will be from about 0.1 g to about 10 g, preferably 0.5 g to 5 g, when given orally. In some instances, a sufficient therapeutic effect can be obtained at lower doses while in others, larger doses will be required. As is apparent to one skilled in clinical pharmacology, the amount of BMY 14802 comprising the daily dose may be given in a single or divided dose, taking into account those principles understood by the skilled practitioner and necessary for his practice of the art.

The term "systemic administration" as used herein refers to oral, sublingual, buccal, transnasal, transdermal, rectal, intramuscular, intravenous, intraventricular, intrathecal, and subcutaneous routes. Generally, it will be found that when a compound of the present invention is administered orally a slightly larger quantity of the active drug may be required to produce the same effect as a somewhat smaller quantity when given parenterally. In accordance with good clinical practice, it is preferred to administer the instant compounds at a concentration level which will produce effective beneficial effects without causing any harmful or untoward side effects.

Therapeutically, the instant compounds are generally given as pharmaceutical compositions comprised of an effective ischemia-protective amount of BMY 14802 or a pharmaceutically acceptable acid addition salt and/or hydrate thereof and a pharmaceutically acceptable carrier. Pharmaceutical compositions for effecting such treatment will contain a major or minor amount (e.g. from 95% to 0.5%) of at least one compound of the present invention in combination with a pharmaceutical carrier, the carrier comprising one or more solid, semi-solid, or liquid diluent, filler and formulation adjuvant which is non-toxic, inert and pharmaceutically acceptable. Such pharmaceutical compositions are preferably in dosage unit forms; i.e., physically discrete units having a pre-determined amount of the drug corresponding to a fraction or multiple of the dose which is calculated to produce the desired therapeutic response. In usual practice, the dosage units contain 1, ½, ⅓, or less of a single dose. A single dose preferably contains an amount sufficient to produce the desired therapeutic effect upon administration at one application of one or more dosage units according to the pre-determined dosage regimen, usually a whole, half, third, or less of the daily dosage administered once, twice, three, or more times a day. It is envisioned that other therapeutic agents can also be present in such a composition. Pharmaceutical compositions which provide from 0.1 to 1 g of the active ingredient per unit dose are preferred and are conventionally prepared as tablets, lozenges, capsules, powders, aqueous or oily suspensions, syrups, elixirs, and aqueous solutions. Preferred oral compositions are in the form of tablets, capsules, and may contain conventional excipients such as binding agents. (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of BMY 14802 with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of BMY 14802 or one of its salt forms in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

When transnasal application is intended, the BMY 14802 pharmaceutical composition is formulated in a pharmaceutical composition which enhances penetration of the nasal mucosa. Such formulations normally employ fatty acid salts of the BMY 14802 base compound and their preparation and use would be known to one skilled in the pharmaceutical arts.

DESCRIPTION OF SPECIFIC EMBODIMENTS

BMY 14802 in the form of the hydrochloride salt was employed in the procedures of the following examples.

EXAMPLE 1

Antagonism of N-Methyl-D-Aspartic Acid-Induced Convulsions

Groups of mice received either a 20 mg/kg s.c. pretreatment of BMY 14802 hydrochloride or no pretreatment. After a 15 minute interval the groups were injected with NMDA i.p. at varying doses and an $ED_{50}$ for NMDA-produced convulsions determined. Pretreatment with BMY 14802 elevated the NMDA $ED_{50}$ from about 98 mg/kg to about 143 mg/kg.

EXAMPLE 2

Protection Against Hypoxia—Induced Death

Groups of rats received either water or drug solution in various doses given i.p. at specified times prior to a 1-minute exposure to a 100% nitrogen atmosphere. This 1-minute nitrogen exposure is lethal within 10 minutes to all animals receiving only vehicle. A 25 mg/kg treatment given 15 minutes before nitrogen exposure protected 3 of 8 animals while giving 50 mg/kg protected all animals. Increasing the time interval between pretreatment and nitrogen exposure to 30 minutes resulted in protection of 4 of 8 animals at 25 mg/kg and 3 of 8 animals at 50 mg/kg. Further increase to a 60 minute time interval resulted in protection of only 2 of 8 animals at 50 mg/kg with no protection at 25 mg/kg.

EXAMPLE 3

Antagonism of N-Methyl-D-Aspartic Acid—Evoked Release of Acetylcholine

Slices of rat striatal brain tissue were preloaded with tritiated choline and the release of tritiated acetylcholine evoked by NMDA in the presence or absence of BMY 14802 hydrochloride is measured. A significant attenuation of acetylcholine release evoked by 0.5 mM NMDA was effected by 50 $\mu$M of BMY 14802 hydrochloride.

From the above examples, it may be concluded that BMY 14802 may be employed prophylactically (Example 2—nitrogen hypoxia test) or therapeutically (Examples 1, 3—against the hypoxia-induced degenerative cascade).

We claim:

1. A process for protecting brain cells from ischemia which comprises administration to a mammal suffering from ischemia or of an effective ischemia-protectant dose of 4-(4(5 fluoro-2-pyrimidinyl)-1-piperazinyl)-1-(4-fluorophenyl)butanol or a pharmaceutically acceptable acid addition salt and/or hydrate thereof.

2. A process for treating ischemia-induced brain disorders in a mammal in need of such treatment, the disorder selected from the group consisting of stroke, seizures, transient ischemic attacks, hypoglycemia, anoxia, asphyxiation or brain injury; the treatment comprising systemic administration to the mammal of an effective dose of BMY 14802 or a pharmaceutically acceptable acid addition salt and/or hydrate thereof.

3. A preoperative process comprising administration of BMY 14802 or a pharmaceutically acceptable acid addition salt and/or hydrate thereof to a mammal prior to a surgical procedure rendering the mammal susceptible to ischemia.

4. The process of claim 2 wherein the disorder is stroke.

5. The process of claim 2 wherein the disorder is seizures.

6. The process of claim 2 wherein the disorder is transient ischemic attacks.

7. The process of claim 2 wherein the disorder is hypoglycemia.

8. The process of claim 2 wherein the disorder is anoxia.

9. The process of claim 2 wherein the disorder is asphyxiation.

10. The process of claim 2 wherein the disorder is brain injury.

11. The process of claim 1 wherein the pharmaceutically acceptable acid addition salt of BMY 14802 is the hydrochloride salt.

* * * * *